United States Patent [19]
Kiselev et al.

[11] 4,027,010
[45] May 31, 1977

[54] ANTISTAPHYLOCOCCOUS HUMAN IMMUNOGLOBULIN AND METHOD OF PREPARING SAME

[76] Inventors: Anatoly Efimovich Kiselev, ulitsa Kostyakova, 8/6, kv. 182; Semen Vladimirovich Skurkovich, Frunzensky val, 38, kv. 103; Tatyana Vasilievna Golosova, ulitsa B. Gruzinskaya, 62, kv. 82; Anatoly Alexandrovich From, ulitsa Flotskaya, 28, korpus 1, kv. 84; Grigory Fedoseevich Papko, Malaya Moskovskaya ulitsa, 27, kv. 8; Ljudmila Semenovna Shenkman, Shmitovsky proezd, 1, kv. 47; Tatyana Pavlovna Anikina, ulitsa Dubninskaya, 39, korpus 3, kv. 44, all of Moscow, U.S.S.R.

[22] Filed: Apr. 15, 1975

[21] Appl. No.: 568,371

[52] U.S. Cl. .......................... 424/87; 260/112 B; 260/112 R
[51] Int. Cl.² ...................................... A61K 39/40
[58] Field of Search ....... 424/87; 260/112 R, 112 B

[56] References Cited
UNITED STATES PATENTS
2,437,060   3/1948   Williams et al. .............. 260/112 B

*Primary Examiner*—Lewis Gotts
*Assistant Examiner*—Cary Owens

[57] ABSTRACT

Antistaphylococcous human immunoglobulin consisting of gamma globulin fraction isolated from the plasma of man immunized with staphylococcous toxoid, containing staphylococcous α-antitoxin in the titre from 50 to 640 Units per ml and agglutinins against staphylococci in the titre to 1:20480 in a physiological or isotonic solution.

The method for preparing said antistaphyloccus human immunoglobulin consists in that the plasma isolated from the blood of donors immunized with staphylococcus toxoid in the doses of 1, 1 and 2 ml, injected at 7-day intervals, is fractionated with ethyl alcohol at subzero temperatures with subsequent isolation of the gamma globulin fraction, its purification, drying and dissolution in physiological or isotonic solution. This immunoglobulin is useful in treating staphylococcal infections.

2 Claims, No Drawings

ANTISTAPHYLOCOCCOUS HUMAN IMMUNOGLOBULIN AND METHOD OF PREPARING SAME

The present invention relates to antistaphylococous human immune globulin and to a method of preparing same.

Antistaphylococcous immune globulin is used in therapy, surgery, pediatrics, obstetrics and gynaecology, otorhinolaryngology, ophthalmology, dermatology, for treating patients with staphylococcous infections (staphylococcous sepsis, septicopyemia, peritonitis, pneumonia, endocarditis, meningitis, staphylococcous destruction of lungs, empyema, osteomyelitis, staphylodermia, staphylococcous affections of ear, nose and throat and also localized acute purulent staphylococcous diseases).

Known in the prior art is method of preparing gamma globulins used in prophylaxis of some infections diseases. It consists in fractionating the plasma of donor blood with ethyl alcohol for which purpose it is cooled to subzero temperatures and an acetate buffer in a 53.3 percent aqueous solution of ethyl alcohol is added to bring the pH of the medium to 7.2. As ethyl alcohol is added, the temperature of the mixture drops to −2.5° − −3° C. The final concentration of ethyl alcohol in the system should be 8 percent. The precipitated fibrinogen is separated by centrifuging. A 53.3 percent solution of alcohol is then added to the supernatant liquid containing the acetate buffer to bring the pH to 6.9 and to attain the final concentration of the alcohol in the mixture of 25 percent. The temperature of the mixture should be about −5° C. The precipitation is repeated two times. The precipitates obtained in the second and third precipitation steps are processed with ethyl alcohol to its final concentration in the mixture of 17 percent, and the pH of 5.2, at a temperature of −6° C. The precipitate is separated and the supernatant liquid and processed with ethyl alcohol until its concentration in the mixture is 17 percent, the pH is 5.2 and the temperature is to −6° C. The precipitate consists mainly of gamma globulins. The precipitate is separated by centrifuging at a temperature of −6° C. The pH of the supernatant fluid is adjusted to 7.4 ±0.2 by adding sodium bicarbonate, and the concentration of ethyl alcohol to 20–25 percent by adding 95 percent ethyl alcohol. The temperature is maintained at about −5° C. The precipitate consists mainly of a more readily soluble part of gamma globulins. The precipitate is centrifuged at a temperature of −5° C and is used to prepare a solution containing 16.5 g of gamma globulins in 100 ml, which is sterilized.

Gamma-globulins obtained by the known method are not specifically active against various infectious diseases and in particular against staphylococcous infections. Said gamma globulins have low titres of antistaphylococcous L-antitoxic antibodies (to 4–10 Units per ml) and cannot therefore be effectively used to protect from staphylococcous infection, in staphylococcous sepsis in particular.

The object of this invention is to prepare antistaphylococcous human immune globulin having specific action against staphylococcous infections.

The object has been accomplished by that antistaphylococcous human immune globulin, containing gamma globulin fraction isolated from the human blood plasma in physiological or isotonic solution, according to the invention, consists of the gamma globulin fraction isolated from the plasam of blood taken from donors immunized with staphylococcous toxoid containing from 50 to 640 Units per ml of staphylococcous α-antitoxin and to 1:20480 of antistaphylococceous agglutinins in the titre. In the method for preparing said immune globulin by fractionating blood plasma with ethyl alcohol at subzero temperatures with subsequent isolation of the gamma globulin fraction, its purification and dissolution in physiological or isotonic solution, according to the invention, use is made of plasma isolated from the blood of donors immunized with staphylococcous toxoid by consecutive injection of 1, 1 and 2 ml doses of the toxoid at 7-day intervals.

The proposed antistaphylococcous human immune globulin has been tested on experimental animals and in clinic on man.

The experimental on animals have shown that the protective effect of antistaphylococcous immune globulin in staphylococcous infection is three times as stronger compared with the known non-specific gamma globulins.

The proposed antistaphylococcous immune globulin has the titre of α-antitoxin from 50 to 640 Units per ml and agglutinins against staphylococci in the tire to 1:20480, which is markedly higher that the titre of α-antitoxin in common gamma globulins, in which the titre of α-antitoxin is from 4 to 10 units per ml.

In accordance with this feature, the protective effect of the antistaphylococcous immune globulin in staphylococcous infections is much higher that with non-specific gamma globulins.

This has been proved by clinical observations in treating patients with staphylococcous sepsis. A single therapeutic dose of the proposed antistaphylococcous immune globulin having the titre of α-antitoxin 100 and more Units per ml was given to children in doses of 3 ml of a 10 percent solution and 6 ml of the same 10 percent solution to adults. The preparation was injected intramuscularly once a day every other or third day. The course of treatment consisted from three to five injections of therapeutic doses of the preparation. In grave cases of generalized staphylococcous infection, up to 10 therapeutic doses were given to the patients.

The observations have shown that under the effect of the antistaphylococcous immune globulin, the body temperature quickly fell in the patients, toxemia decreased, the acute course of staphylococcous sepsis was aborted, and the general condition of the patients improved significantly. Blood findings gradually normalized, and pathologic staphylococci were absent in the blood of patients in repeated inoculations after the completion of the therapeutic course. We observed 50 patients with staphylococcous sepsis. The group comprised 35 children and 15 adults. Out of the 35 children the specific therapy with antistaphylococcous immune globulin was given to 26 prematurely born neonates and to nine children of various age. Staphylococcous sepsis in the observed patients was very grave.

The specific therapy with antistaphylococcous immune globulin proved effective in 40 cases out of 50. Out of the 10 lethal cases two patients died from acute leukemia and burns (the main disease).

The total lethality of staphylococcous sepsis is 16 percent, while according to the literature, the mortality rate in cases with staphylococcous sepsis treated by complex therapy incorporating antibiotics is 50–70 percent.

The method of preparing said immune globulin is realized as follows.

Volunteering donors, ageing from 20 to 40 and meeting all other blood-giving and plasmapheresis requirements are selected. If the hematological and biochemical indices are normal, the donors are immunized with adsorbed staphylococcous toxoid by subcutaneous injections under the scapula with doses of 1, 1 and 2 ml at a 7-day interval. In 7 days, on the termination of the immunization course, the serum of the donor blood is analyzed for the presence of staphylococcous α-antitoxin. Donors having the titre of the staphylococcous α-antitoxin not below 5 Units per ml of blood serum are allowed to undergo plasmapheresis for preparing hyperimmune antistaphylococcous plasma.

The concentration of staphylococcous α-antitoxin in the serum of the blood of the donors immulized with staphylococcous toxoid, is determined by the neutralization of lysis of rabbit erythrocytes.

In this reaction, use is made of a method of neutralization of hemolytic properties of staphylococcous α-toxin, the Lh of which is accurately determined.

Plasmapheresis is effected according to the known method. Antistaphylococcous plasma is obtained in sterile closed system which is forced in twin-wall plastic bags.

Plasmapheresis is accomplished with donors from two to four times a month at 7–14 day intervals. To about 250 ml of immune antistaphylococcous plasma are obtained from a donor at a single session. The immune plasma is kept before fractination in the frozen state in plastic bags at a temperature of −20° to −30° C.

Before extracting the gamma globulin fraction from the antistaphylococcous plasma, the plasma is fractionated with ethyl alcohol at low temperatures (below zero).

Fibrinogen is isolated at the first fractionation step.

The second step of fractionation is precipitation of globulins, during which the main bulk of beta and gamman globulins is precipitated.

The precipitated fraction containing, in addition to gamma and beta globulins, also prothrombin, profibrinolysin and other proteins, is used for furter fractionation.

Prothrombin is isolated at the third fractionation step.

The precipitates of the second and the third steps are suspended in an equal volume of a 2 percent solution of sodium chloride cooled to the temperature of 0° C.

Next, 1.5 volume (by weight of the precipitate) of distilled water, cooled to 0° C, is added to the obtained suspension. The pH of the suspension as adjusted to 5.0–5.1.

To that end, the volume of the mixture is measured and an acetate buffer solution cooled to 0° C is added with stirring, taking 1.5 liter of the buffer solution per liter of the susension (11.5 ml of 2M $CH_3COOH$, 11.5 ml of 2M $CH_3COONa$)

The mixture is kept at a temperature of 0° C for 12 hours to precipitate prothrombin which is then separated on a supercentrifuge at 20,000 rpm, at a temperature of 0° C. The centrifugate is used for preparing immune globulin and fibrinolysin.

Antistaphylococcous immune globulin is isolated at the fourth and fifth steps of the fractionation process.

An equal volume of a 26 percent solution of alcohol, cooled to a temperature of −3° C, is added to the centrifugate at a temperature of 0° C. The pH of the mixture is adjusted to 5.0–5.1 by adding 1M solution of NaOH or 1M solution of HCl. As the alcohol is added the temperature of the mixture falls from 0 to −4° C. In these conditions, beta globulin, lipoids, profibrinolysin and a small part of gamma globulins are precipitated. The precipitate is separated on a supercentrifuge at a temperature of −4° C and is used to prepared fibrinolysin. The centrifugate is filtered through paper pulp at a temperature of −3° to −5° C to obtain a clear filtrate.

A 1M solution of $NaHCO_3$ is used to bring the pH of the medium in the clear filtrate to 6.9–7.0, and then a 96 percent solution of alcohol, cooled to a temperature of −15° C, is added in the quantity of 0.16 liter per liter of the solution which results in the final concentration of the alcohol in the solution of 25 percent. The temperature of the mixture should be −9° C. In these conditions the immune globulin precipitates from the solution and is separated on a supercentrifuge. The grey precipitate of purified immune globulin is weighed, dissolved in a sterile physio-logical solution at a ratio of 1 : 1.5, filled into vials of 500 ml capacity in 200 ml portions, frozen at a temperature of −35° to −40° C and dried lyophylically. A 10 percent solution is then prepared from the immune globulin, for which purpose the dry power is dissolved in apyrogenic distilled water taken in the quantity equal to that of physiological solution added to the dry precipitate before drying it.

0.9 g of sodium chloride is added per 100 g of dry powder.

The concentration of protein in the obtained solution is determined on a refractometer and is adjusted to 10 percent by weight (±1 percent) with physiological solution, whenever necessary.

Thus prepared solution is filtered through paper pulp and finally, in sterile conditions, through sterilizing ceramic material in vacuum. The sterile solution is filled in ampoules in 3-ml portions, and sealed.

The yield of antistaphylococcous ammune globulin is 8–10 doses per liter of plasma.

The finished preparation is tested for protein content, pyrogens, toxicity, and purity of the fraction by electrophoresis on paper.

The obtained antistaphylococcous immune globulin is a clear, or slightly opalescing, colourless or slightly yellowing solution.

Antistaphylococcous immune globulin should be specific, sterile, non-toxic and pyrogen-free. Its titre is not less than 50 Units of antistaphylococcous anti-alpha-toxic anti-bodies per ml (according to the reaction of neutralization of hemolytic action of the staphylococcous alpha-toxin on rabbit erythrocytes). The protein content of the solution of antistaphylococcous immune globulin should be 10 ±1 percent. The gamma globulin fraction content, as determined electrophoretically, should be not less than 97 percent of the total protein.

For a better understanding of the invention, the following example of its practical embodiment is given by way of illustration.

EXAMPLE

Volunteer donors ageing from 20 to 40 are selected for obtaining antistaphylococcous immune globulin from them and examined for conformance with the medical requirements for blood giving and plasmapheresis. The donors are then immunized with adsorbed staphylococcous toxoid with doses of 1, 1 and 2 ml at 7-day intervals between the injections. If staphylococcous α-antitoxin in the donor blood is equal to or exceeds 5 Units per ml (neutralization of hemolytic properties of staphylococcous α-toxin) the donors are admitted for the plasmapheresis operation for preparing and accumulating the required quantities of hyperimmune antistaphylococcous plasma. The obtained plasma is kept before the fractionation in plastic bags in the frozen state at a temperature of −20° to −30° C.

In order to isolate the gamma globulin fraction, 10 l of said hyperimmune antistaphylococcous plasma are processed with ethyl alcohol until the concentration of the alcohol in the plasma is 8 percent, at a temperature of −3° C, and the pH of 7.2. Fibrinogen is precipitated, as a result, and separated.

The supernatant solution is processed with ethyl alcohol until its concentration in the mixture is 25 percent, at a temperature to −5° C and the pH 6.9. A precipitate, containing the main bulk of beta and gamma globulins falls out, is separated, and the supernatant liquid is again processed with ethyl alcohol. Precipitates of the second and the third precipitation steps (500 g) are suspended in 500 ml of a 2 percent solution of sodium chloride cooled to 0° C. 750 ml of distilled water, cooled to 0° C, are added to the obtained suspension and the volume of the obtained mixture is measured. Now an acetate buffer solution (11.5 ml of a 2M $CH_3COOH$ 11.5 ml of a 2M $CH_3COONa$), cooled to 0° C, is added to the mixture in the quantity of 1.5 liter per liter of the suspension. The pH of the suspension is adjusted to 5–5.1.

The mixture is kept at a temperature of 0° C for 12 hours. Prothrombin precipitates in these conditions, and is separated on a centrifuge at 20,000 rpm at a temperature of 0° C.

The centrifugate (4 liters) is processed with an equal volume of a 26 percent solution of alcohol cooled to 3° C; the pH of the mixture is adjusted to 5–5.1 by adding a 1M solution of NaOH or a 1M solution of HCl. As alcohol is added, the temperature of the mixture fall from 0° C to −4° C.

In these conditions, beta-globulins, lipoids, profibrinolysin and a small part of gamma globulins precipitate. The precipitate is separated on a centrifuge at a temperature of −4° C and used to isolate fibrinolysin. The centrifuate is filtered through paper pulp at a temperature of −3° to −5° C to obtain a clear filtrate. The pH of the filtrate is adjusted to 6.9–7.0 by adding a 1M solution of $NaHCO_3$, and alcohol (96 percent), cooled to −15° C, is added in the quantity of 0.16 liter per liter of the solution, as a result of which the alcohol concentration in the solution becomes 25 percent. The temperature of the mixture should be −9° C. In these conditions, immune globulin is precipitated and separated.

The damp precipitate of the purified immune globulin, in the quantity of 150 g, is dissolved in sterile physiological solution at a ratio of 1:1.5, and filled in 200 ml portions into 500-ml vials. The solution is frozen at a temperature of −35° to −40° C and dried lyophylically. The dry antistaphylococcous immune globulin is used to prepare a 10 or a 16 percent solution in pyrogen-free distilled water.

0.9 g of sodium chloride is added per 100 g of the dry powder. The protein content of the obtained solution is determined refractometrically and adjusted with physiological solution to 10%±1 whenever required. The obtained solution is filtered through paper pulp and then, in sterile conditions, through ceramic material in vacuum. The sterile solution of antistaphylococcous immune globulin is filled in 3-ml portions into vials, and sealed. The yield of antistaphylococcous immune globulin is 800–100 doses per ten liters of the immune plasma.

In the obtained batches of the preparation, one ml of the antistaphylococcous immune globulin contains from 50 to 640 antitoxic units and agglutinins against staphylococci 1:20480. The issued batches of antistaphylococcous immune globulin are sterile, non-toxic and posses specific activity.

What we claim is:

1. Antistaphylococcus human immunoglobulin consisting of the gamma globulin fraction isolated from the plasma of blood of man immunized with staphylococcus toxoid, containing staphylococcus α-antitoxin in the titre from 50 to 640 Units per ml and agglutinins against staphylococci in the titre to 1:20480.

2. Antistaphylococcus human immunoglobulin composition consisting of the gamma globulin fraction isolated from the plasma of blood of man immunized with staphylococcus toxoid, containing staphylococcus α-antitoxin in the titre from 50 to 640 Units per ml and agglutinins against staphylococci in the titre to 1:20480, in a physiological or isotonic solution.

* * * * *